(12) United States Patent
Lee et al.

(10) Patent No.: US 8,460,394 B2
(45) Date of Patent: Jun. 11, 2013

(54) GRIPPING MECHANISM

(75) Inventors: Wei-Chen Lee, Taipei (TW); Chih-Wei Wu, Taipei County (TW)

(73) Assignee: National Taiwan University of Science and Technology, Taipei (TW)

( * ) Notice: Subject to any disclaimer, the term of this patent is extended or adjusted under 35 U.S.C. 154(b) by 258 days.

(21) Appl. No.: 12/844,836

(22) Filed: Jul. 28, 2010

(65) Prior Publication Data

US 2011/0270416 A1  Nov. 3, 2011

(30) Foreign Application Priority Data

May 3, 2010 (TW) .................................. 99114081 A

(51) Int. Cl.
*A61F 2/54* (2006.01)
*B25J 15/10* (2006.01)
(52) U.S. Cl.
USPC ................................. 623/64; 294/111; 901/39
(58) Field of Classification Search
CPC ............ A61F 2/588; B25J 15/10; B25J 15/103
USPC .................... 623/63–65; 294/111; 901/39
See application file for complete search history.

(56) References Cited

U.S. PATENT DOCUMENTS 999,484 A * 8/1911 Carnes ............................. 623/62
4,367,891 A * 1/1983 Wauer et al. .................. 294/197

FOREIGN PATENT DOCUMENTS

SU            848021      * 7/1981

* cited by examiner

*Primary Examiner* — David H Willse
(74) *Attorney, Agent, or Firm* — Jianq Chyun IP Office

(57) ABSTRACT

A gripping mechanism for gripping an object includes a base, a first gripping module, a second gripping module, and a driving device. The first gripping module is disposed on the base and has at least one receiving slot. The second gripping module is movably disposed in the receiving slot. The driving device is disposed on the base and connected to the first gripping module and the second gripping module. The driving device is operable to drive the first gripping module to switch between an opened state and a closed state, or drive the second gripping module to move relative to the first gripping module to enable the gripping mechanism to grip or release the object.

5 Claims, 6 Drawing Sheets

GRIPPING MECHANISM

CROSS-REFERENCE TO RELATED APPLICATION

This application claims the priority benefit of Taiwan application serial no. 99114081, filed on May 3, 2010. The entirety of the above-mentioned patent application is hereby incorporated by reference herein and made a part of this specification.

BACKGROUND OF THE INVENTION

1. Field of the Invention

The present invention relates to a gripping mechanism, and more particularly, to a gripping mechanism with both claw and finger.

2. Description of Related Art

Nowadays, physically handicapped people caused by an industrial accident or Force Majeure usually need a prosthesis to perform the function of the disabled parts in order to alleviate inconvenience in daily life and work.

Currently commercially available prosthetic hand is usually in the form of a claw or an under-actuated finger. Electromyographic effect of muscles is used to control a motor in the prosthesis for transmission as people's hand, when performing gripping or releasing actions, drives muscles at different positions of the arm (e.g. inner side or outer side of the arm) to operate, to achieve closing or opening actions of the prosthesis.

The claw-type gripping mechanism is a mechanism driven by a motor in a single degree of freedom causing two gripping members to move in opposite directions. Such a claw-type gripping mechanism has the advantages of rapid response speed, simple structure, low cost and large gripping force. However, such claw-type gripping mechanism has poor outer appearance and stability and can only be used to grip objects with a regular outer profile.

On the other hand, the under-actuated-finger-type gripping mechanism can be adapted to objects with various different outer profiles by simulating the movements of human fingers. Although involving movements in multiple degrees of freedom, such under-actuated-finger-type gripping mechanism has a poor gripping force and a slow movement speed due to the nature of the driving manner.

SUMMARY OF THE INVENTION

Accordingly, the present invention is directed to a gripping mechanism which can be adapted to objects with various different outer profiles.

In one embodiment, the present invention provides a gripping mechanism for gripping an object. The gripping mechanism includes a base, a first gripping module, a second gripping module, and a driving device. The first gripping module is disposed on the base and has at least one receiving slot. The second gripping module is movably disposed in the receiving slot. The driving device is disposed on the base and connected to the first gripping module and the second gripping module. The driving device is operable to drive the first gripping module to switch between an opened state and a closed state, or drive the second gripping module to move relative to the first gripping module to enable the gripping mechanism to grip or release the object.

In one embodiment of the present invention, when the driving device drives the first gripping module to move to an intermediate position during switching from the opened state toward the closed state, the driving device drives the second gripping module to move out of the receiving slot.

In one embodiment of the present invention, the first gripping module is substantially a claw having at least two gripping arms. The gripping arms are interconnected with one another and are pivotably connected to the base. The at least one of the gripping arms has the receiving slot.

In one embodiment of the present invention, the gripping mechanism further includes a linking rod pivotably connected between any two adjacent gripping arms. The driving device is connected to and operable to drive one of the gripping arms so as to drive the other of the gripping arms to move relatively through the linking rod.

In one embodiment of the present invention, the second gripping module includes at least one finger, and the object is adapted to be substantially gripped between the finger and the linking rod.

In one embodiment of the present invention, the finger includes at least two finger sections and a roller. The finger sections are pivotably connected to one another. The roller is disposed between the finger sections. The driving device comprises a motor and a connecting member, one end of the connecting member is connected to the motor, and the other end of the connecting member is connected to the roller.

In view of the forgoing, in the embodiment of the present invention, the gripping mechanism has the second gripping module movably received in the receiving slot of the first gripping module, such that the gripping mechanism can grip or release the object using the first gripping module or the second gripping module. This allows the gripping mechanism to have the function of the two different types of gripping modules and allows the user to decide one suitable gripping module in accordance with the outer profile of the object, thus expanding the application scope of the gripping mechanism.

Other objectives, features and advantages of the present invention will be further understood from the further technological features disclosed by the embodiments of the present invention wherein there are shown and described preferred embodiments of this invention, simply by way of illustration of modes best suited to carry out the invention.

DESCRIPTION OF THE EMBODIMENTS

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purposes of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component or one or more additional components are between "A" component and "B" component. Also, the description of "A" component "adjacent to" "B" component herein may contain the situations that "A" component is directly "adjacent to" "B" component or one or more additional components are between "A" component and "B" component. Accordingly, the drawings and descriptions will be regarded as illustrative in nature and not as restrictive.

Figure 1:
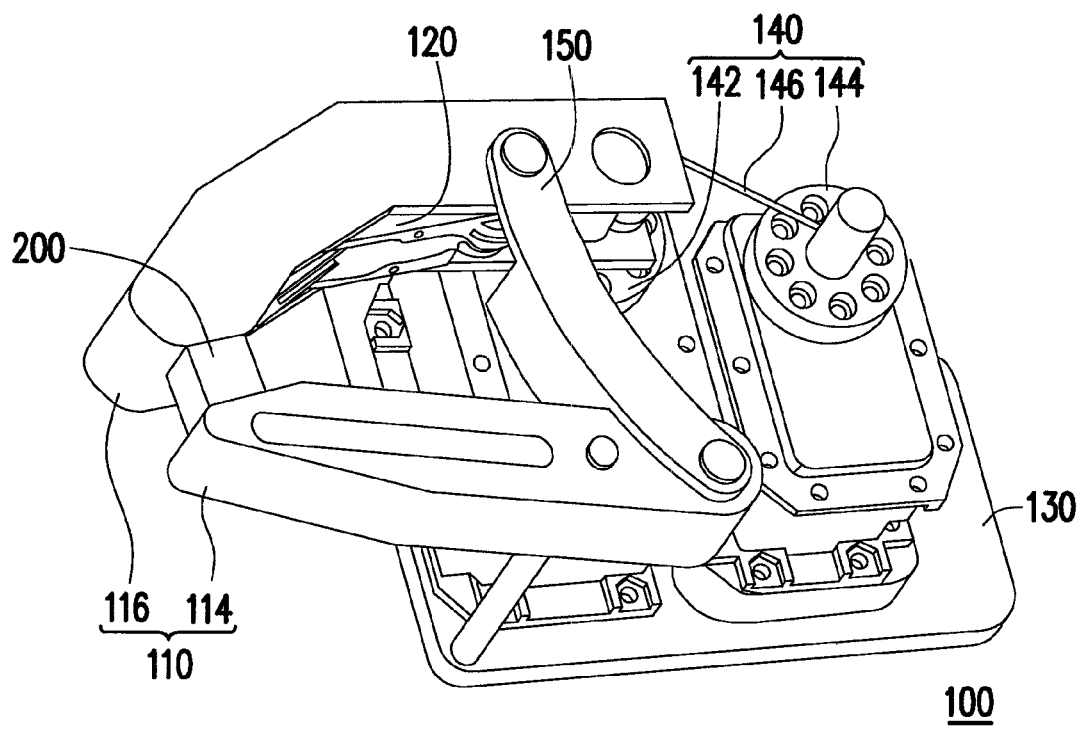
FIG. 1 illustrates a gripping mechanism according to one embodiment of the present invention.
Figure 2:
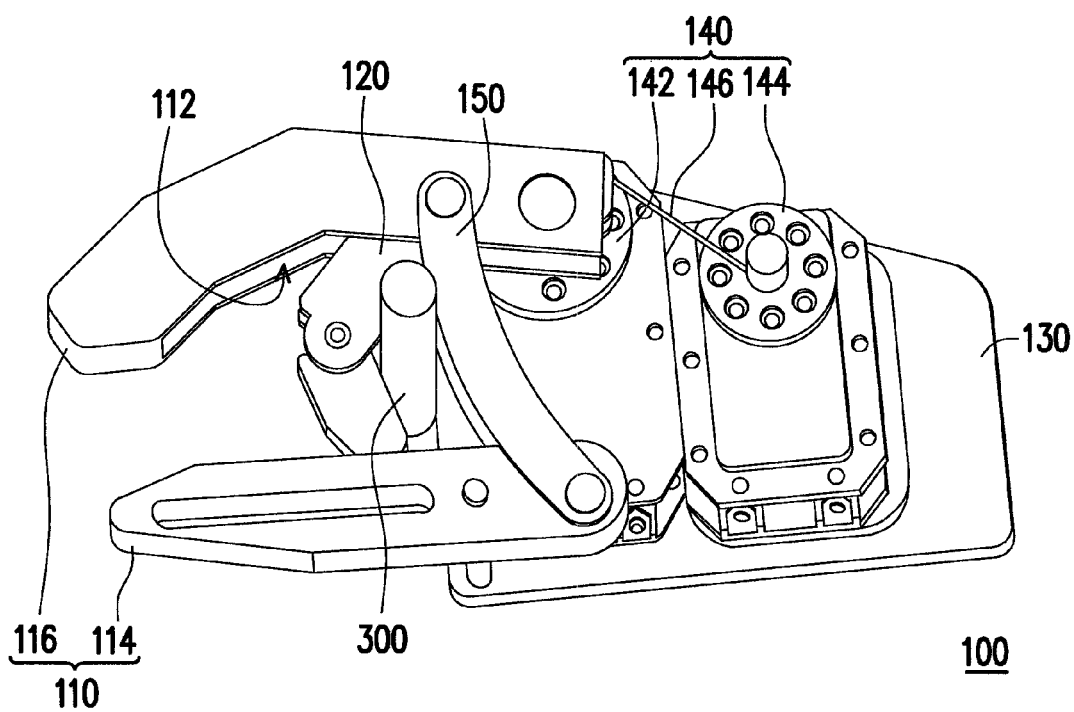
FIG. 2 illustrates the gripping mechanism of FIG. 1 which grips an object having another outer profile.

FIG. 1 illustrates a gripping mechanism according to one embodiment of the present invention. FIG. 2 illustrates the gripping mechanism of FIG. 1 which grips an object having another outer profile. Referring to FIG. 1 and FIG. 2, in the present embodiment, the gripping mechanism 100 is adapted for use in a prosthesis to function as a hand. The gripping mechanism 100 includes a first gripping module 110, a second gripping module 120, a base 130, and a driving device 140. The first gripping module 110 is disposed on the base 130 and has a receiving slot 112. The second gripping module 120 is movably disposed in the receiving slot 112. The driving device 140 is disposed on the base 130 and connected to the first gripping module 110 and the second gripping module 120. As such, the driving device 140 may drive the first gripping module 110 to perform opening or closing actions, or drive the second gripping module 120 to move relative to the first gripping module 110 to enable the gripping mechanism 100 to grip or release an object 200 or 300.

With the configuration described above, the gripping mechanism 100 may integrate the two different types of gripping modules 110, 120 together by disposing the second gripping module 120 in the receiving slot 112 of the first gripping module 110. As such, the user may decide to use which one of the gripping modules 110, 120 in accordance with the outer profile of the object to be gripped. Therefore, the gripping mechanism 100 can be adapted to objects of various outer profiles, thus expanding the application scope of the gripping mechanism 100.

Figure 3A:
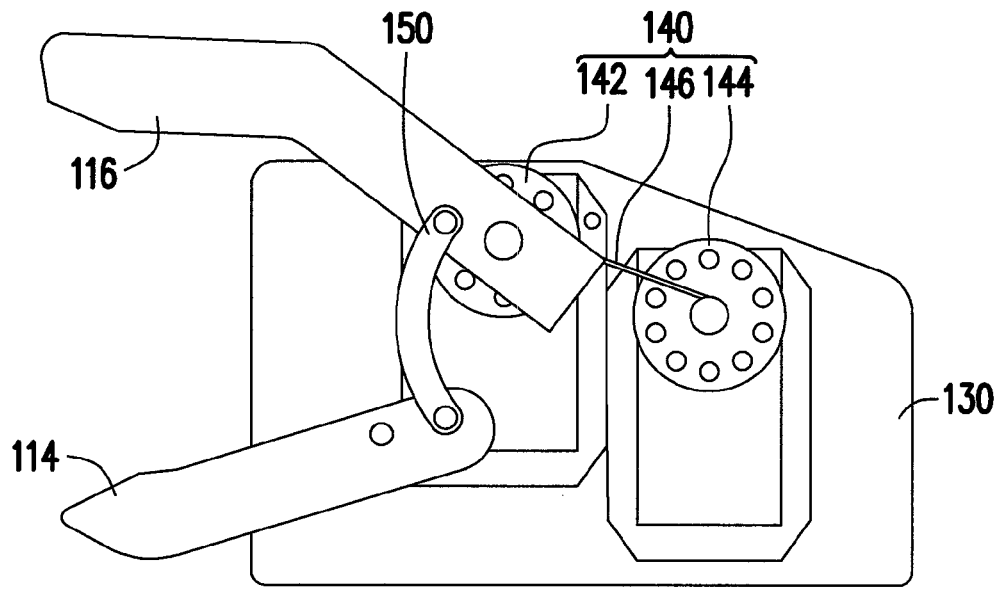
FIGS. 3A to 3C are operational views of the first gripping module of the gripping mechanism of FIG. 1.
Figure 3B:
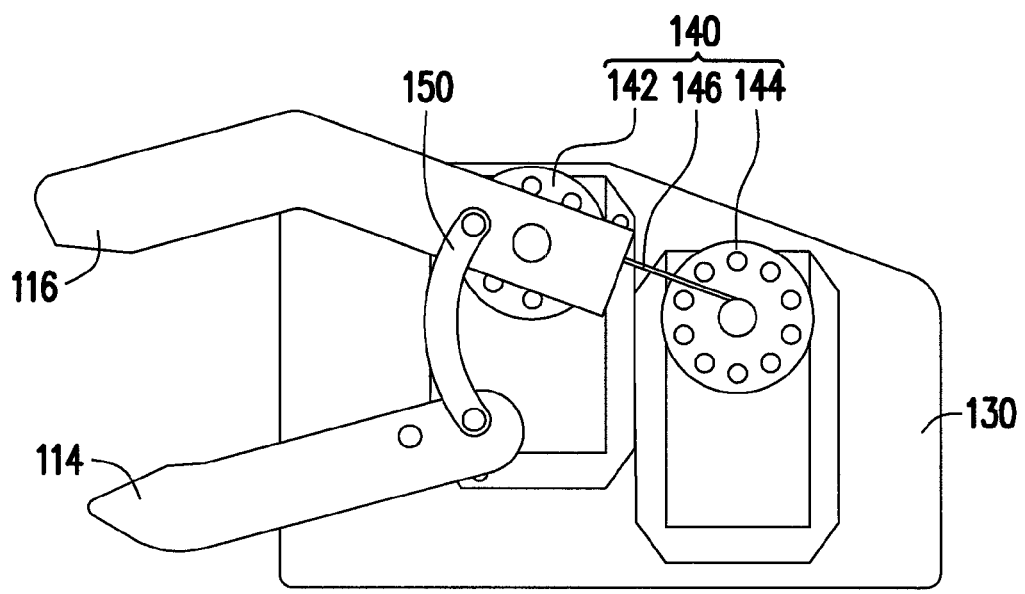
Figure 3C:
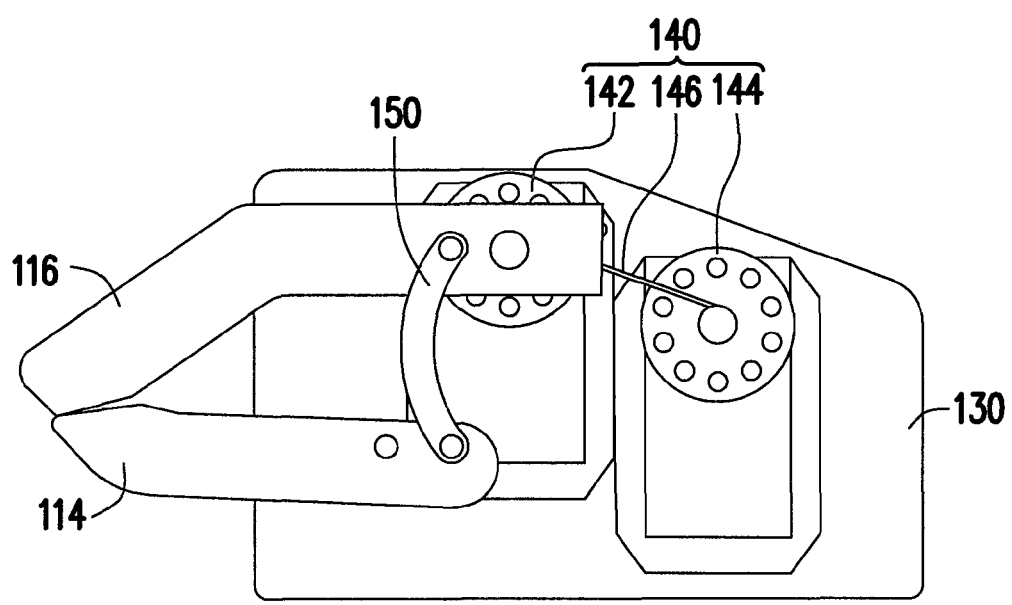

FIGS. 3A to 3C are operational views of the first gripping module of the gripping mechanism of FIG. 1. Referring to FIG. 1 and FIGS. 3A to 3C, specifically, in the present embodiment, the driving apparatus 140 includes a first motor 142, a second motor 144, and a connecting member 146. The first gripping module 110 is essentially a claw having two gripping arms 114, 116. The gripping arm 114 is pivotably disposed on the base 130, and the gripping arm 116 is connected to the first motor 142. In addition, the gripping mechanism 100 further includes a linking rod 150 pivotably connected between the two gripping arms 114, 116. As such, the first gripping module 110 is implemented as a link mechanism. When the first motor 142 drives the gripping arm 116 to swing, the gripping arm 116 can drive the gripping arm 114 to swing in an opposite direction through the linking rod 150, such that the gripping arms 114, 116 can move relatively, thus enabling the first gripping module 110 to switch between an opened state shown in FIG. 3A and a closed state shown in FIG. 3C for gripping or releasing an object 200.

Figure 4A:
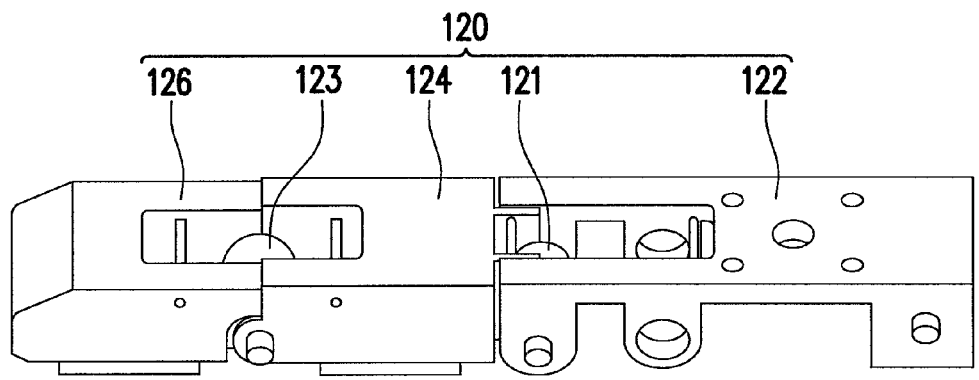
FIG. 4A and FIG. 4B are partial views of the second gripping module of the gripping mechanism of FIG. 2 with the second gripping module in a stretched state, viewed from different aspects, respectively.
Figure 4B:
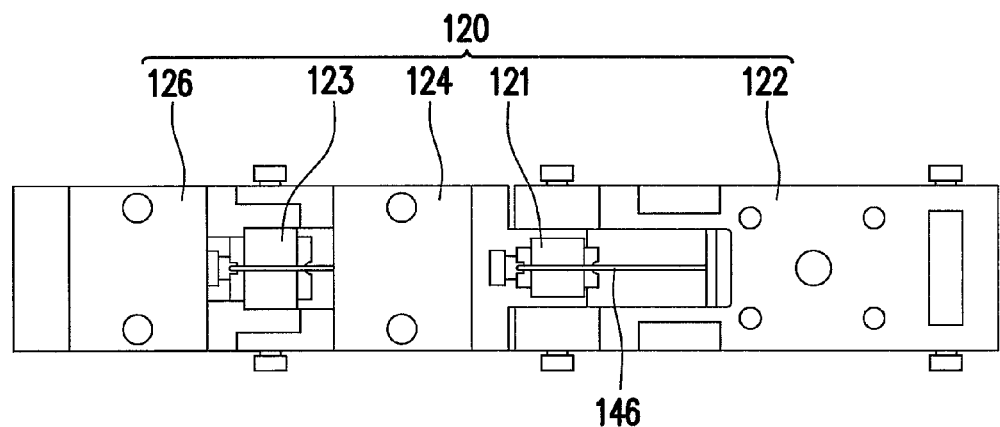
Figure 4C:
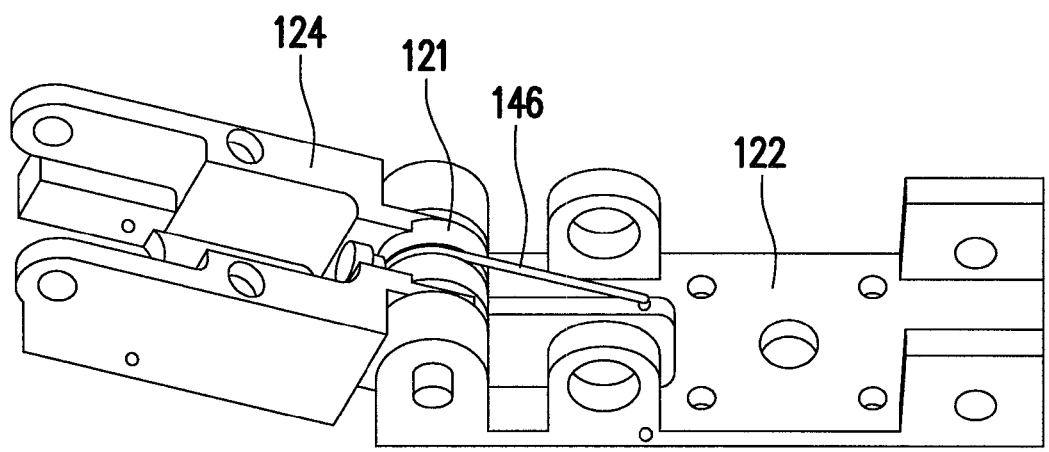
FIG. 4C is a partial view of the second gripping module of FIG. 4A with the second gripping module in a bent state.

FIG. 4A and FIG. 4B are partial views of the second gripping module of the gripping mechanism of FIG. 2 with the second gripping module in a stretched state, viewed from different aspects, respectively. FIG. 4C is a partial view of the second gripping module of FIG. 4A with the second gripping module in a bent state. Referring to FIG. 2 and FIGS. 4A to FIG. 4C, in the present embodiment, the second gripping module 120 is substantially implemented as an under-actuated finger, which includes a first finger section 122, a second finger section 124 and a third finger section 126 that are pivotably connected with one another, a first roller 121 pivotably connected between the first finger section 122 and the second finger section 124, and a second roller 123 pivotably connected between the second finger section 124 and the third finger section 126. The first finger section 122 is pivotably connected to the gripping arm 116 of the first gripping module 110. In addition, one end of the connecting member 146 (e.g. a rope) of the driving device 140 is connected to the second motor 144, and the other end is connected to the first roller 121 or the second roller 123. First taking the first roller 121 as an example, as shown in FIG. 4C, the first roller 121 is substantially pivotably connected to the first finger section 122 and secured to the second finger section 124. As such, once the second motor 144 drives the connecting member 146, the connecting member 146 drives the first roller 121 to pivot, thus making the second finger section 124 bend relative to the first finger section 122. Like driving structures are also disposed between the second finger section 124 and the third finger section 126 in the same manner, and therefore explanation thereof is not repeated herein.

In the present embodiment of the gripping mechanism 100, an under-actuated finger (i.e. the second gripping module 120) is disposed in a gripping arm 116 of the claw (i.e. the first gripping module 110). The claw has the advantages of rapid gripping speed and large gripping force, whereas the under-actuated finger is capable of gripping objects with an irregular outer profile. Referring again to FIGS. 1 and 2, to grip the object 200 with a regular outer profile or an object with a large weight using the gripping mechanism 100, the user may drive the first gripping module 110 to grip that object. On the other hand, to grip, for example, the object 300 of FIG. 2 that has an irregular outer profile just like the object 300 with curved shape, the user may drive the second gripping module 120 to grip that object 300. As such, the single gripping mechanism 100 can grip objects with various different outer profiles, thereby meeting different needs of gripping.

It is noted that the present embodiment does not limit the structure and number of the first gripping module 110 and the second gripping module 120, i.e. does not limit the number of the claw or under-actuated finger in the gripping mechanism 100. Other configurations are well within the scope of the present invention as long as the second gripping module 120 is received in the receiving slot 112 of the first gripping module 110 and can move relative to the first gripping module 110 such that the gripping mechanism 100 can grip objects selectively using the first gripping module 110 or the second gripping module 120.

Referring again to FIGS. 1 and 2, it is noted that, since the second gripping module 120 is disposed in the receiving slot 112 of the first gripping module 110 in the present embodiment, once the gripping arm 116 of the first gripping module 110 swings, it drives the second gripping module 120 to swing at the same time. In addition, the major difference between the first gripping module 110 and the second gripping module 120 is that the driving response time of the claw-type first gripping module 110 is shorter than that of the under-actuated-finger-type second gripping module 120. To grip the object 300, the user may first drive the first gripping module 110 to move from the opened state toward the closed state to an intermediate position (as shown in FIG. 2), and then drive the second gripping module 120 to move out of the receiving slot 112 to grip the object 300. As such, the gripping efficiency of the gripping mechanism 100 can be enhanced.

On the other hand, as shown in FIG. 2, in the present embodiment, when the second gripping module 120 grips the object 300, the gripped object 300 is substantially gripped between the second gripping module 120 and the linking rod 150. That is, in addition to being used as a linking element between the gripping arms 114 and 116, the linking rod 150 can also be used to support the object 300 to increase the stability of the second gripping module 120 when gripping the object 300.

In summary, in the embodiment of the present invention, the gripping mechanism has the second gripping module received in the receiving slot of the first gripping module, such that the user can decide the gripping module of the integrated gripping mechanism to be driven in accordance with the outer profile of the object. This makes the gripping mechanism have the functions of both the claw-type and under-actuated-finger-type gripping modules.

In addition, when moving, the claw-type gripping module also moves the finger received in its receiving slot. Therefore, the user may first move the received finger to an appropriate position by the rapid moving claw and then drive the finger to move relative to the claw to grip the object.

Furthermore, the linking rod that links the gripping arms of the claw-type gripping module can also be used as part of the finger-type gripping module to provide an abutting surface to thereby increase the reliability of the finger-type gripping module when gripping objects.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A gripping mechanism for gripping an object, comprising:
   a base;
   a first gripping module disposed on the base, wherein the first gripping module is a claw having at least two gripping arms, the gripping arms are interconnected with one another and are pivotably connected to the base, and at least one of the gripping arms has a receiving slot;
   a second gripping module movably disposed in the receiving slot; and
   a driving device disposed on the base and connected to the first gripping module and the second gripping module, the driving device being operable to drive the first gripping module to switch between an opened state and a closed state, and drive the second gripping module to move relative to the first gripping module to enable the gripping mechanism to grip or release the object, wherein the second gripping module moves out of the receiving slot at an intermediate position between the opened state and the closed state to grip the object.

2. The gripping mechanism according to claim 1, wherein when the driving device drives the first gripping module to move to an intermediate position during switching from the opened state toward the closed state, the driving device drives the second gripping module to move out of the receiving slot.

3. The gripping mechanism according to claim 1, further comprising a linking rod pivotably connected between any two adjacent gripping arms, wherein the driving device is connected to and operable to drive one of the gripping arms so as to drive the other of the gripping arms to move in an opposite direction through the linking rod.

4. The gripping mechanism according to claim 3, wherein the second gripping module includes at least one finger, the finger comprising:
   at least two finger sections that are pivotably connected to one another; and
   a roller disposed between the finger sections, wherein the driving device comprises a motor and a connecting member, one end of the connecting member is connected to the motor, and the other end of the connecting member is connected to the roller.

5. The gripping mechanism according to claim 4, wherein the object is adapted to be substantially gripped between the finger and the linking rod.

* * * * *